United States Patent
Kuhara et al.

(10) Patent No.: US 9,591,988 B2
(45) Date of Patent: Mar. 14, 2017

(54) MAGNETIC RESONANCE IMAGING APPARATUS AND MAGNETIC RESONANCE IMAGING METHOD

(75) Inventors: Shigehide Kuhara, Otawara (JP); Shuhei Nitta, Tokyo (JP); Tomoyuki Takeguchi, Tokyo (JP); Nobuyuki Matsumoto, Tokyo (JP)

(73) Assignee: TOSHIBA MEDICAL SYSTEMS CORPORATION, Otawara-shi, Tochigi (JP)

( * ) Notice: Subject to any disclaimer, the term of this patent is extended or adjusted under 35 U.S.C. 154(b) by 0 days.

(21) Appl. No.: 13/287,268

(22) Filed: Nov. 2, 2011

(65) Prior Publication Data
US 2012/0108946 A1 May 3, 2012

(30) Foreign Application Priority Data
Nov. 2, 2010 (JP) .................. 2010-245745

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0037* (2013.01); *A61B 5/0044* (2013.01);
(Continued)

(58) Field of Classification Search
CPC ..... A61B 5/0037; A61B 5/0044; A61B 5/055; A61B 5/0456; G01R 33/543; G01R 33/4833; G01R 33/5673
See application file for complete search history.

(56) References Cited

U.S. PATENT DOCUMENTS 6,381,296 B1 * 4/2002 Nishiura ..................... 378/4
6,771,999 B2    8/2004 Salla et al.
(Continued)

FOREIGN PATENT DOCUMENTS

CN    101081165 A    12/2007
JP    01-134580 A    5/1989
(Continued)

OTHER PUBLICATIONS

Chris Rorden. MRIcro manual and tutorial. retrieved Apr. 18, 2013 from <http://www.mccauslandcenter.sc.edu/mricro/mricro/index.html>.*

(Continued)

*Primary Examiner* — Long V Le
*Assistant Examiner* — Colin T Sakamoto
(74) *Attorney, Agent, or Firm* — Nixon & Vanderhye P.C.

(57) ABSTRACT

According to one embodiment, a MRI apparatus includes an acquisition unit, a reference section information calculating unit, a positioning unit and an imaging unit. The acquisition unit acquires frames of section image data including a heart from an object with use of magnetic resonance. The reference section information calculating unit calculates spatial positional information of a reference section of the heart based on the frames of the section image data. The positioning unit displays a reference section image of the heart on a display unit and performs positioning of an imaging part for imaging through the displayed reference section image of the heart. The reference section image is calculated from the frames of the section image data based on the positional information of the reference section. The imaging unit images the imaging part set by the positioning.

32 Claims, 6 Drawing Sheets

(51) Int. Cl.
- *G01R 33/483* (2006.01)
- *G01R 33/54* (2006.01)
- *A61B 5/0456* (2006.01)
- *G01R 33/567* (2006.01)

(52) U.S. Cl.
CPC ....... *G01R 33/4833* (2013.01); *G01R 33/543* (2013.01); *A61B 5/0456* (2013.01); *G01R 33/5673* (2013.01)

(56) References Cited

U.S. PATENT DOCUMENTS

| | | |
|---|---|---|
| 7,280,862 B2 | 10/2007 | Gupta et al. |
| 7,684,604 B2 | 3/2010 | Bystrov et al. |
| 7,966,055 B2 | 6/2011 | Guehring et al. |
| 8,213,699 B2 | 7/2012 | Wakai et al. |
| 2005/0033143 A1 | 2/2005 | O'Donnell et al. |
| 2005/0113664 A1 | 5/2005 | Stefani et al. |
| 2008/0009709 A1 | 1/2008 | Guehring et al. |
| 2012/0126812 A1 | 5/2012 | Nitta et al. |
| 2012/0134566 A1 | 5/2012 | Nitta et al. |

FOREIGN PATENT DOCUMENTS

| | | |
|---|---|---|
| JP | 04-218139 A | 8/1992 |
| JP | 2003-325514 A | 11/2003 |
| JP | 2004-181246 | 7/2004 |
| JP | 2005-087237 A | 4/2005 |
| JP | 2005-152656 | 6/2005 |
| JP | 2006-055641 | 3/2006 |
| JP | 2007-319689 | 12/2007 |
| JP | 2009-028515 | 2/2009 |
| WO | WO 2010052629 A1 * | 5/2010 |

OTHER PUBLICATIONS

Rybicki et al., "Principles and clinical applications of single-shot magnetic resonance imaging". Supplement to Applied Radiology. Apr. 2001.*

Cho et al., Foundations of Medical Imaging. John Wiley & Sons. 1993. pp. 303-305, Figs. 11-4 and 11-5.*

University of Virginia "Short Axis View". archived Jul. 15, 2007, retrieved Sep. 22, 2014 from <https://web.archive.org/web/20070715050625/http://www.med-ed.virginia.edu/courses/rad/cardiacmr/Anatomy/Short.html>.*

University of Virginia "Horizontal Long Axis View". archived Jul. 15, 2007, retrieved Sep. 22, 2014 from < https://web.archive.org/web/20070715050027/http://www.med-ed.virginia.edu/courses/rad/cardiacmr/Anatomy/Horizontal.html>.*

CMR Image Acquisition Protocols, Version 1.0, pp. 1-16 (Mar. 2007).

Office Action issued Jan. 22, 2014, in CN Patent Application No. 201110340656.4.

Office Action issued Apr. 21, 2015, in CN Patent Application No. 201110340656.4.

Office Action issued May 1, 2015 in JP Patent Application No. 2011-226294.

* cited by examiner

MAGNETIC RESONANCE IMAGING APPARATUS AND MAGNETIC RESONANCE IMAGING METHOD

CROSS REFERENCES TO RELATED APPLICATIONS

This application is based upon and claims the benefit of priority from Japanese Patent Application No. 2010-245745 filed on Nov. 2, 2010; the entire content of Japanese Patent Application No. 2010-245745 is incorporated herein by reference.

FIELD

Embodiments described herein relate generally to a MRI (magnetic resonance imaging) apparatus and a magnetic resonance imaging method.

BACKGROUND

MRI is an imaging method which excites nuclear spins of an object set in a static magnetic field with an RF (radio frequency) signal having the Larmor frequency and reconstructs an image based on MR (magnetic resonance) signals generated due to the excitation.

Examination methods of a heart by MRI include morphological observation by imaging features of a heart, observation of myocardial dynamic states (wall motion) by cine imaging, observation of perfusion states of blood flow by imaging myocardial blood flow perfusion with contrast medium, observation of myocardial viability by late contrast-enhanced imaging which performs imaging after a predetermined period elapses after injecting contrast medium, 3D (three dimensional) observation of a whole coronary artery by non-contrast enhanced imaging of the coronary artery with enhancing contrasts of blood flow and myocardium, and the like.

Imaging for a cardiac examination requires use of reference cross sections based on cardiac anatomical characteristics. The reference cross section images include various section views such as a vertical long-axis view, a horizontal long-axis view, a 2 chamber long-axis view, a 3 chamber long-axis view, a 4 chamber long-axis view and a LV (left ventricle) short-axis view in addition to axial images, coronal images and sagittal images for positioning a ROI (region of interest) and the like.

A Cardiac imaging by MRI needs acquisition of these reference cross section images at first. However, time and labor are necessary for positioning to acquire the reference cross section images because of the complex cardiac structure. Specifically, positioning a reference cross section image with reference to another reference cross section image and imaging of a positioned cross section are repeated with setting axial images as initial reference cross section images. Accordingly, more detailed procedures are prescribed as the standardized protocol for standardization of the cardiac imaging.

On the other hand, some techniques which support the positioning of the reference cross section images for cardiac imaging are suggested. For example, there is a suggested technique that 3D WH MRCA (Whole Heart MR Coronary Angiography) data is acquired so that the reference cross section images can be positioned with use of MPR (multi planar reconstructions) image data generated by MPR processing of the acquired 3D WH MRCA data. In this method, shortening of scan time is expected since imaging is not required for positioning each reference cross section image.

As another example, there is a suggested method that many axial images which cover a heart entirely are acquired by multi-slice imaging to manually set landmarks on some axial images while observing the axial images by a user. For example, landmarks are set by a user to positions of the center of aorta, the apex cordis, the mitral valve and the like on an axial image. Then, the reference cross sections necessary for cardiac imaging are automatically calculated with reference to the set landmarks.

In order to position the reference cross sections for cardiac imaging, it is necessary to repeat an imaging scan according to the number of the reference cross section images. Consequently, the work operation for positioning the reference cross sections requires time and impedes improvement of throughput in a heart examination. In addition, accuracy in positioning depends on user skill. That is, sufficient knowledge and experiment with regard to the cardiac anatomical positions are required for positioning the reference cross sections with satisfactory accuracy.

It is an object of the present invention to provide a magnetic resonance imaging apparatus and a magnetic resonance imaging method which make it possible to image a heart by positioning respective reference cross sections in the heart with practical accuracy more easily in a shorter time.

DETAILED DESCRIPTION

Figure 1:
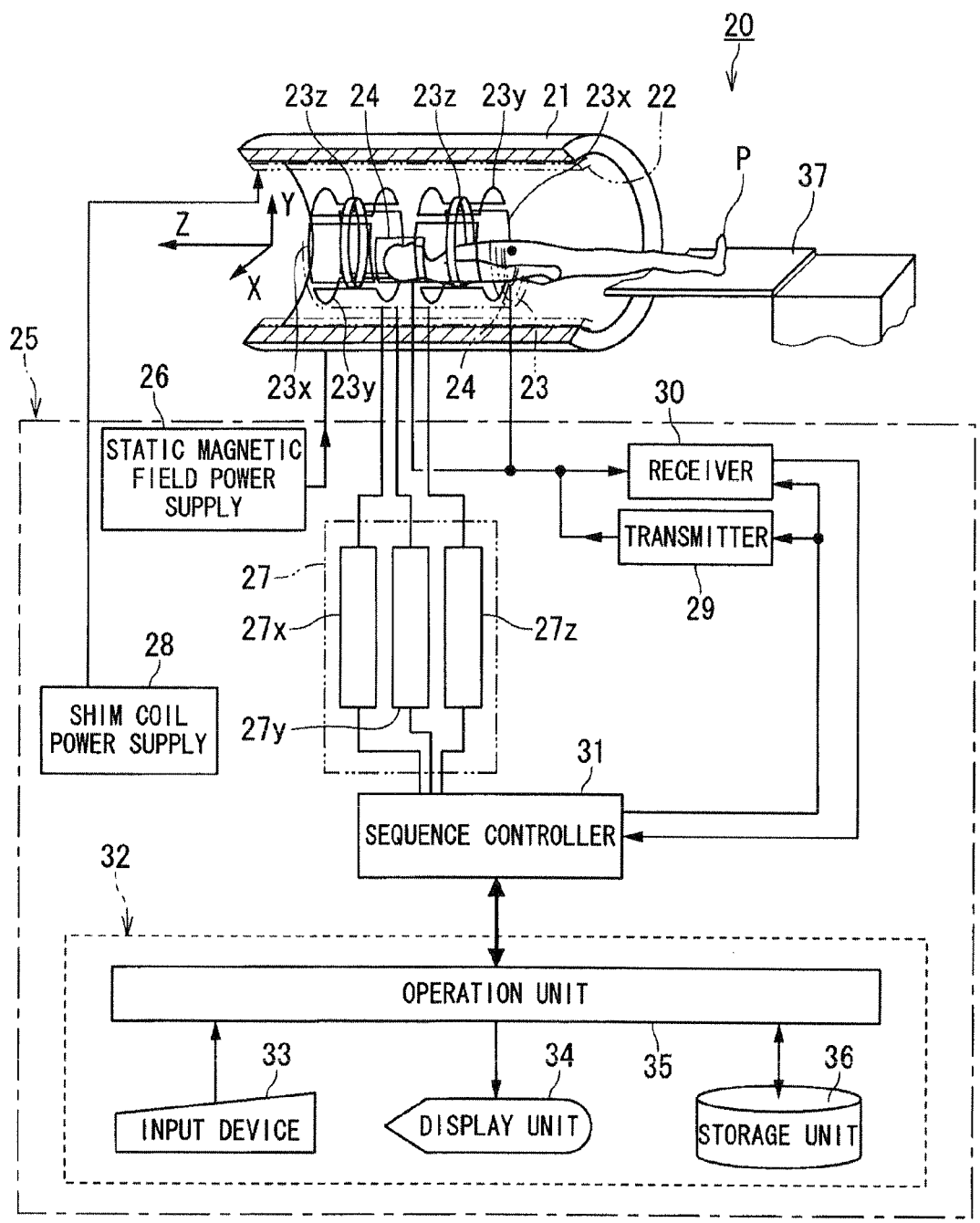
FIG. 1 is a block diagram showing an embodiment of a magnetic resonance imaging apparatus according to the present invention.

In general, according to one embodiment, a magnetic resonance imaging apparatus includes an acquisition unit, a reference section information calculating unit, a positioning unit and an imaging unit. The acquisition unit is configured to acquire frames of section image data including a heart from an object with use of magnetic resonance. The reference section information calculating unit is configured to calculate spatial positional information of a reference section of the heart based on the frames of the section image data. The positioning unit is configured to display a reference section image of the heart on a display unit and perform positioning of an imaging part for imaging through the displayed reference section image of the heart. The reference section image is calculated from the frames of the section image data based on the positional information of the reference section. The imaging unit is configured to image the imaging part set by the positioning.

In addition, a magnetic resonance imaging apparatus according to an embodiment includes an acquisition unit, a reference section information calculating unit, a positioning unit and an imaging unit. The acquisition unit is configured to acquire frames of section image data including a heart from an object with use of magnetic resonance The reference section information calculating unit is configured to calculate positional information of characterized parts of the heart based on the frames of the section image data. The positioning unit is configured to display a reference section image of the heart on a display unit based on the positional information of the characterized parts and perform positioning of an imaging part for imaging through the displayed reference section image of the heart. The imaging unit is configured to image the imaging part set by the positioning.

In addition, a magnetic resonance imaging apparatus according to an embodiment includes a reference section information calculating unit, a positioning unit and an imaging unit. The reference section information calculating unit is configured to calculate positional information of characterized parts of a heart based on volume data including the heart of an object with use of magnetic resonance. The positioning unit is configured to display a reference section image of the heart on a display unit based on the positional information of the characterized parts and perform positioning of an imaging part for imaging through the displayed reference section image of the heart. The imaging unit is configured to image the imaging part set by the positioning.

In addition, a magnetic resonance imaging method according to an embodiment includes acquiring frames of section image data including a heart from an object with use of magnetic resonance, calculating spatial positional information of a reference section of the heart based on the frames of the section image data, displaying a reference section image of the heart on a display unit and performing positioning of an imaging part for imaging through the displayed reference section image of the heart, and imaging the imaging part set by the positioning. The reference section image is calculated from the frames of the section image data based on the positional information of the reference section.

Embodiments of a magnetic resonance imaging apparatus and a magnetic resonance imaging method according to the present invention will be described with reference to the accompanying drawings.

FIG. 1 is a block diagram showing an embodiment of a magnetic resonance imaging apparatus according to the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with at least one of the transmitter 29 and the receiver 30. The transmission RF coil 24 has a function to transmit a RF signal given from the transmitter 29 to the object P. The reception RF coil 24 has a function to receive a MR signal generated due to an nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and an RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27.

The sequence controller 31 is also configured to give raw data to the computer 32. The raw data is complex data obtained through the detection of a MR signal and A/D (analog to digital) conversion to the MR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

In addition, an ECG (electro cardiogram) unit 38 for acquiring an ECG signal of the object P is provided with the magnetic resonance imaging apparatus 20. The ECG signal detected by the ECG unit 38 is outputted to the computer 32 through the sequence controller 31.

Note that, a PPG (peripheral pulse gating) signal representing a beat as pulse wave information may be acquired instead of an ECG signal representing a beat as heart rate information. A PPG signal is acquired by detecting a pulse wave of e.g. tip of a finger as an optical signal. When a PPG signal is acquired, a PPG signal detection unit is provided with the magnetic resonance imaging apparatus 20.

The computer 32 gets various functions by the operation unit 35 executing some programs stored in the storage unit 36 of the computer 32. Alternatively, some specific circuits having various functions may be provided with the magnetic resonance imaging apparatus 20 instead of at least a part of the programs.

Figure 2:
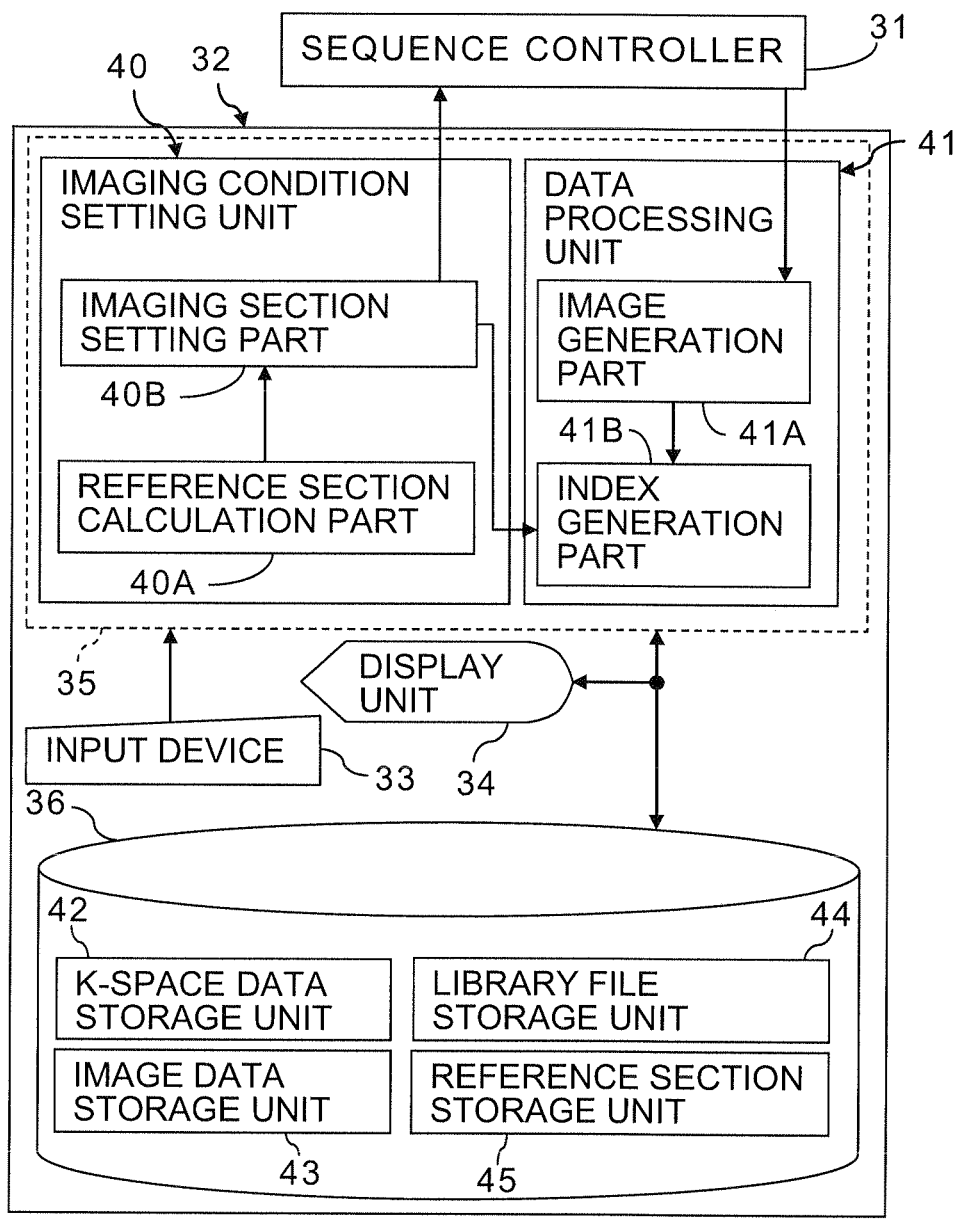
FIG. 2 is a functional block diagram of the computer shown in FIG. 1.

FIG. 2 is a functional block diagram of the computer 32 shown in FIG. 1.

The operation unit 35 of the computer 32 functions as an imaging condition setting unit 40 and a data processing unit 41 by executing the programs stored in the storage unit 36. Meanwhile, the storage unit 36 functions as a k-space data storage unit 42, an image data storage unit 43, a library file storage unit 44 and a reference section storage unit 45. Further, the imaging condition setting unit 40 includes a reference section calculation part 40A and an imaging section setting part 40B. Meanwhile, the data processing unit 41 includes an image generation part 41A and an index generation part 41B.

The imaging condition setting unit 40 has a function to set imaging conditions including a pulse sequence and output the set imaging conditions to the sequence controller 31 to the control sequence controller 31. Especially, the imaging condition setting unit 40 has a function to set imaging conditions for cardiac imaging.

The reference section calculation part 40A has a function to automatically generate cardiac reference cross section image data or reference cross section information for generating the cardiac reference cross section image data by calculation based on one of three simple orthogonal cross section pieces of image data such as pieces of axial image data, pieces of coronal image data or pieces of sagittal image data including a heart acquired from an object P. That is, the reference section calculation part 40A has a function to calculate spatial positional information of reference sections of a heart based on simple frames of section image data such as axial image data. The spatial positional information of the reference sections of the heart may be not only the cardiac reference cross section image data itself but vector information.

Note that, the reference section calculation part 40A may be configured to automatically generate the cardiac reference cross section image data or the reference cross section information for generating the cardiac reference cross section image data with use of all or two of the pieces of axial image data, the pieces of coronal image data and the pieces of sagittal image data. In other words, spatial positional information of cardiac reference sections can be calculated based on frames of section image data consisting of at least one of axial image data, coronal image data and sagittal image data including the heart.

Alternatively, spatial positional information of cardiac reference sections can be also calculated based on 3D imaging data such as 3D WH MRCA data involving the heart of the object. That is, the reference section calculation part 40A has a function to calculate spatial positional information of cardiac reference sections based on volume data obtained from frames of section image data, 3D imaging data and the like including a heart of an object.

The cardiac reference cross section images include mainly six images of a vertical long-axis view, a horizontal long-axis view, a 2 chamber long-axis view, a 3 chamber long-axis view, a 4 chamber long-axis view and a LV short-axis view. These images are used for functional evaluation of a LV. However, the present embodiment can apply to a case of functional evaluation of a RV (right ventricle) and a case of functional evaluation of a valve such as a mitral valve or a tricuspid valve. In case of functional evaluation of a RV, reference cross sections are sections involving a LV. For example, the reference cross sections are sections crossing a RV in the above-mentioned 2 chamber view or a 3 chamber view. In case of functional evaluation of a valve such as a mitral valve, reference cross sections are sections passing through the valve. For example, the reference cross sections are sections passing through a mitral valve and orthogonal to the above-mentioned 3 chamber view.

These cardiac reference cross section images are mainly used for positioning an imaging part in cardiac imaging and as indexes for sorting cardiac images. Therefore, desired kinds of reference cross section image data selected according to a diagnostic purpose and an imaging part by a user are automatically calculated by the reference section calculation part 40A. Especially, it is important to calculate spatial positional information with regard to at least three and above mutually different reference sections out of the above mentioned cardiac reference sections for positioning of an imaging part.

The cardiac reference cross section images are conventionally acquired by chain oblique imaging which repeats six to eight procedures including positioning based on axial images and imaging. Therefore, it is preferable to generate the cardiac reference cross section images based on pieces of axial image data in view of convenience for a user. Accordingly, description will be made for an example case of generating the cardiac reference cross section images based on frames of axial image data as example of frames of simple section image data hereinafter.

The library file storage unit 44 stores pieces of library file data representing determination reference for specifying positions of reference parts of heart such as the apex cordis and the mitral valve in image data as combinations of parameters. Therefore, the reference section calculation part 40A referring to the library files stored in the library file storage unit 44 functions as a determination unit for determining a reference part of heart such as the apex cordis from image data.

Each library file expresses a cardiac anatomical feature as a combination of parameters. The respective library files can be made based on cardiac anatomical knowledge and pieces of image data of cardiac features of many objects. For example, a combination of parameters consisting of each library file can be calculated by so called learning theory based on information representing many cardiac features for respective diseases.

Specifically, a library file can be made of multidimensional vector information consisting of signal values at respective points, gradients between respective signal values, histogram information of signal values and gradients, and the like with regard to an ambit including a characterized part to be specified (e.g., a mitral valve and a blood region surrounding the mitral valve when a part to be specified is the mitral valve) and a region consisting of myocardium or the like.

Generating many pieces of library file data to store the pieces of library file data in the library file storage unit 44 allows the reference section calculation part 40A to be used as the determination unit (identification unit) for determining each reference part of heart such as the apex cordis. In other words, the respective library files stored in the library file storage unit 44 can be used as reference data for calculating the reference cross section image data by the reference section calculation part 40A.

That is, the reference section calculation part 40A can perform detection processing of positional information of cardiac reference sections based on simple frames of section image data such as axial image data or volume image data generated from simple frames of section image data with referring to reference data generated from at least one of anatomical knowledge and frames of cardiac feature image data of other objects. However, the reference section calculation part 40A can be provided with a function to perform detection processing of positional information of cardiac reference sections without referring to the reference data made as the library file data. For example, detection processing of positional information of cardiac reference sections can be also performed by signal processing, based on anatomical knowledge, of simple frames of section image data such as axial image data or volume image data generated from simple frames of section image data.

Accordingly, either detection processing of positional information of cardiac reference sections with referring to reference data or one by signal processing may be selected according to desired conditions. As a specific example, there is a way that detection processing of positional information of the reference sections is performed by the first algorithm including signal processing based on anatomical knowledge and the detection processing is performed by the second algorithm referring to reference data generated from at least one of anatomical knowledge and frames of cardiac feature image data of other objects according to detection accuracy of the positional information of the reference sections by the first algorithm.

Further, other examples include a method for specifying positions of reference cross sections by signal processing based on anatomical knowledge after narrowing down picks of the positions of the reference cross sections by referring to the reference data. As described above, detection processing of positional information of cardiac reference sections can be performed based on frames of section image data or volume image data generated from frames of section image data by the first or the second algorithm.

Note that, it is possible to add a library file based on new data of cardiac feature of an object or new anatomical knowledge in the library file storage unit 44. Therefore, accuracy in reference data can be improved by accumulating library files in the library file storage unit 44. The library file storage unit 44 may add a library file based on cardiac feature image data acquired with another image diagnostic apparatus such as another magnetic resonance imaging apparatus or an X-ray CT (computed tomography) apparatus. On the contrary, some library files stored in the library file storage unit 44 can be outputted to an exterior portion via a network or a storage medium to be used in the exterior portion.

The reference section storage unit 45 has a function to store the cardiac reference cross section image data or spatial positional information of reference cross sections for generating the cardiac reference cross section image data from 3D image data, which are calculated by the reference section calculation part 40A.

The imaging section setting part 40B has a function to set an imaging section to be imaged. The set up of an imaging section can be performed through cardiac reference cross section image data stored in the reference section storage unit 45 or cardiac reference cross section image data which can be generated based on spatial positional information of reference cross sections stored in the reference section storage unit 45. That is, the imaging section setting part 40B has a function to display cardiac reference cross section images with a screen for setting an imaging section on the display unit 34 and set an imaging region through the cardiac reference cross section images displayed on the screen for setting an imaging section according to information from the input device 33.

For example, the imaging section setting part 40B may be configured to display different reference section images generated by calculation as thumbnail images on the display unit 34 and set a data acquisition section by a pulse sequence used to acquire MR data for imaging according to information for selecting a thumbnail image obtained from an input device 33.

In addition, the imaging section setting part 40B is configured to retrieve and acquire scout image data, necessary for positioning pieces of axial image data, from the image data storage unit 43. Note that, a GUI (Graphical User Interface) technique can be used for set up of an imaging part through a screen.

The data processing unit 41 has a function to acquire MR data from the sequence controller 31 to arrange the acquired MR data as k-space data in k-space formed in the k-space data storage unit 42, a function to acquire k-space data from the k-space data storage unit 42 to generate image data, a function to perform necessary image processing and data processing of image data to write the processed image data in the image data storage unit 43 and a function to perform necessary image processing and data processing of image data acquired from the image data storage unit 43 to display the processed image data on the display unit 34.

The image generation part 41A has a function to apply image reconstruction processing including FT (Fourier transform) and necessary image processing to k-space data acquired from the k-space data storage unit 42 to write the processed data in the image data storage unit 43.

The k-space data storage unit 42 has a function to store k-space data outputted from the sequence controller 31. The image data storage unit 43 has a function to store image data generated by the image generation part 41A.

The index generation part 41B has a function to add identification information of a cardiac reference cross section image, which had been used for positioning cardiac image data acquired by an imaging scan, to the image data as sorting information of the image data. That is, the index generation part 41B has a function to add information specifying one of the cardiac reference cross section images, generated by the reference section calculation part 40A, to image data as incidental information. The information for identifying a cardiac reference cross section image corresponding to image data can be acquired from the imaging section setting part 40B. Note that, vector information indicating a position and direction of reference cross section may be used for the identification information.

Then, the operation and action of the magnetic resonance imaging apparatus 20 will be described.

Figure 3:
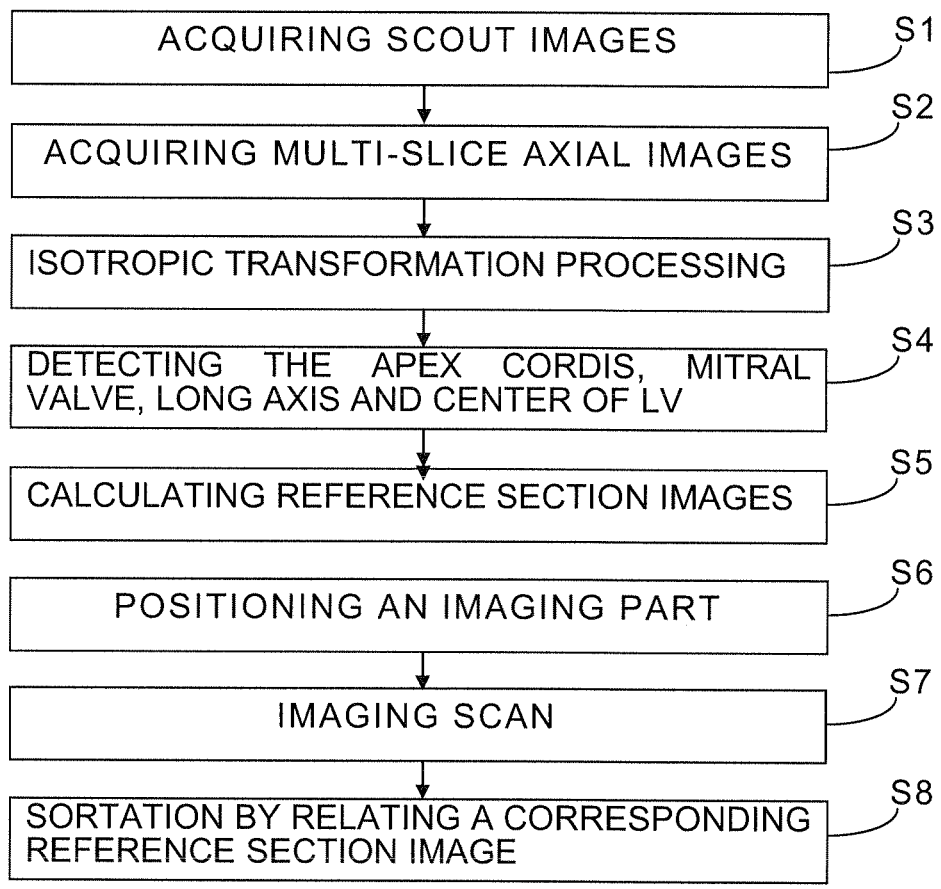
FIG. 3 is a flowchart showing a flow for imaging the heart of the object with automatic calculation of reference cross section images of the heart by the magnetic resonance imaging apparatus shown in FIG. 1.
Figure 4:
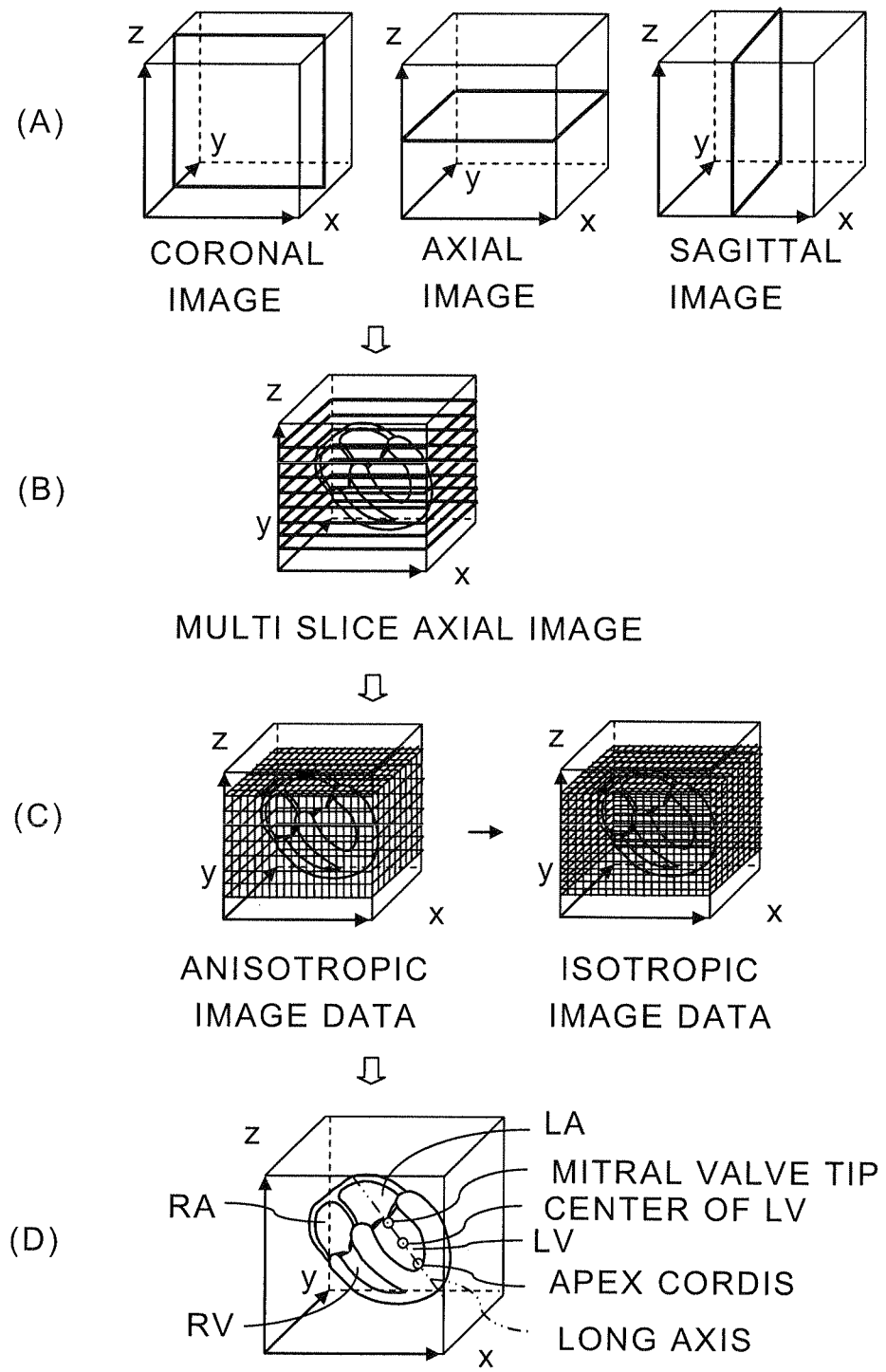
FIG. 4 is a chart showing a procedure for generating cardiac reference cross section image data in the reference section calculation part shown in FIG. 2.

FIG. 3 is a flowchart showing a flow for imaging the heart of the object P with automatic calculation of reference cross section images of the heart by the magnetic resonance imaging apparatus 20 shown in FIG. 1. FIG. 4 is a chart showing a procedure for generating cardiac reference cross section image data in the reference section calculation part 40A shown in FIG. 2.

Firstly, the object P is set to the bed 37 in advance, and a static magnetic field is generated at an imaging area of the magnet 21 (a superconducting magnet) for static magnetic field excited by the static-magnetic-field power supply 26. Further, the shim-coil power supply 28 supplies current to the shim coil 22, thereby uniformizing the static magnetic field generated at the imaging area.

Then, in the step S1, scout image data including the heart of the object P is acquired. Specifically, the imaging section setting part 40B sets an axial section, a coronal section and a sagittal section involving at least the heart of the object P as imaging sections. Then, the imaging condition setting unit 40 sets imaging conditions including a pulse sequence for acquiring MR data from the axial section, the coronal section and the sagittal section and outputs the set imaging conditions to the sequence controller 31 to control the sequence controller 31.

Then, the sequence controller 31 drives the gradient power supply 27, the transmitter 29, and the receiver 30 in accordance with the imaging conditions, thereby generating a gradient magnetic field at the imaging area having the set object P, and further generating RF signals from the RF coil 24. Consequently, the RF coil 24 receives MR signals generated due to nuclear magnetic resonance in the object P. Then, the receiver 30 receives the MR signals acquired with use of magnetic resonance from the RF coil 24 and supplies the MR signals to the sequence controller 31. The sequence controller 31 outputs the MR signals to the data processing unit 41.

Next, the data processing unit 41 arranges the MR data as k-space data in k-space formed in the k-space data storage unit 42. The image generation part 41A applies image reconstruction processing to the k-space data acquired from the k-space data storage unit 42. Consequently, axial image data, coronal image data and sagittal image data of the object P are generated. The generated axial image data, coronal image data and sagittal image data are written in the image data storage unit 43.

Next, the imaging section setting part 40B acquires the axial image data, the coronal image data and the sagittal image data from the image data storage unit 43 to display the image data as scout images on the display unit 34. Consequently, an axial image, a coronal image and a sagittal image involving the heart of the object P as shown in FIG. 4(A) are displayed on the display unit 34. FIG. 4(A) shows an example where the body axis direction vertical to the axial section, the direction vertical to the coronal section and the direction vertical to the sagittal section are set to z axis direction, y axis direction and x axis direction, respectively.

Next, in the step S2, multi-slice axial image data covering the whole heart as shown in FIG. 4(B) is acquired. Specifically, the imaging section setting part 40B sets a range covering the heart as an acquisition region of frames of axial image data through the scout images shown in FIG. 4(A). Subsequently, the frames of axial image data are acquired and written in the image data storage unit 43 in a flow similarly to that in acquisition of the scout image data.

Note that, it is preferable that the MR data for generating the axial image data is acquired in synchronization with an ECG signal acquired from the ECG unit 38 so that shapes of the heart are mutually identical between the respective axial images.

Figure 5:
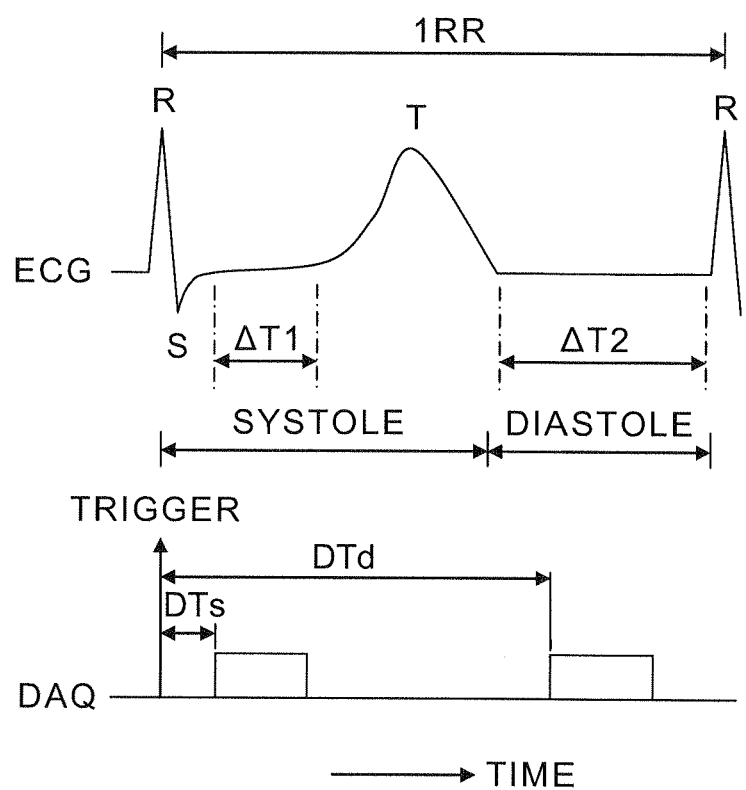
FIG. 5 is; a chart showing acquisition timings of MR signals for generating frames of axial image data as shown in FIG. 4(B)

FIG. 5 is a chart showing acquisition timings of MR signals for generating frames of axial image data as shown in FIG. 4(B).

In FIG. 5, the abscissa axis denotes time, ECG denotes a wave of ECG signal and DAQ denotes duration of data acquisition of MR signals. As shown in FIG. 5, an ECG signal shows reference waves such as R waves, S waves and T waves. Each cardiac systole appears after an R wave while each diastole appears after a systole. Each systole and diastole has a static period $\Delta T1$ and $\Delta T2$ in which variation in the ECG signal becomes stable because the motion of myocardium almost rests respectively.

For that reason, it is important to acquire MR data for frames of axial image data repeatedly at cardiac time phases which can be considered as the same in static periods of systoles or static periods of diastoles of a heart while keeping delay times DTd or DTs from R waves as triggers on the ECG signal constant by ECG gating imaging as shown in FIG. 5. In this case, one frame of axial image data is acquired between adjacent two or three reference waves on the ECG signal, i.e., 1RR or 2RRs, wherein RR denotes an interval between adjacent R waves.

These conditions for data acquisition make it possible to prevent occurrence of deviance in cardiac time phase between frames of axial image data and acquire necessary frames of axial image data in one breath holding. Further, it is possible to make a cardiac shape stable between frames of axial image data by acquiring the frames of the axial image data in static periods of diastoles or systoles of the heart.

In addition, it is important to acquire MR signals for each frame of axial image data by a single shot sequence which acquires MR signals for one frame after applying one excitation pulse in view of preventing influence by respiratory motion.

Next, in the step S3, the reference section calculation part 40A reads the axial image data from the image data storage unit 43 to perform processing to transform the axial image data into isotropic data. When a distance between slices of the axial image data is rougher than a resolution in a slice, the axial image data becomes image data having anisotropy as shown on the left side of FIG. 4(C). Accordingly, isotropic image data consisting of data on isotropic lattice points is generated based on values on the respective points of the anisotropic image data. Generating the isotropic image data can be performed by interpolation processing and processing which removes unnecessary points.

Then, 3D volume image data covering the heart is generated from the multi-slice axial image data by the isotropic transformation processing.

Next, in the step S4, the reference section calculation part 40A detects positions of the apex cordis, the mitral valve, the long axis and the center of left ventricle based on the respective pixel values of the image data after the isotropic transformation processing. Every heart has the four chambers of the RV, the RA (right atrium), the LA (left atrium) and the LV as shown in FIG. 4(D). The mitral valve sectionalizes the LA and the LV. The long axis can be detected as a line segment between the tip of the mitral valve and the apex cordis. The center of LV can be detected as the middle point between the tip of the mitral valve and the apex cordis. Therefore, the positions of the tip of the mitral valve and the apex cordis are firstly detected as initial reference points from the isotropic image data automatically.

The automatic detection of the initial reference points can be performed by one or some of three ways including (1) signal value calculation processing, (2) calculation while referring to reference data and (3) pattern matching. The signal value calculation processing includes detection of the maximum pixel value based on anatomical knowledge, calculation of gradients in pixel values and the like. The reference data includes library files made based on known information such as information with regard to anatomical features of respective cardiac parts and many pieces of cardiac geometrical data acquired from other objects. Note that, each library file consists of multidimensional vector information including signal values, gradients between signal values and histogram information thereof with regard to data in an adjacent region involving a part to be specified as described above.

For example, the cardiac initial reference points can be automatically and analytically detected by detecting a part having large pixel values from the volume image data based on the anatomical knowledge that signal values from blood flow in the aorta up to the LV and the apex cordis have continuity when the axial image data has been acquired under conditions for enhancing signals from blood flow.

More specifically, a search range for the aorta is firstly determined on a certain frame of axial image data obtained from the volume image data based on the known information with regard to spatial position of the aorta. Next, the position showing the maximum pixel value is detected within the search range. Subsequently, points each having the maximum pixel value are tracked in the axial direction. Then, the detected points are mutually connected to obtain the center line of the aorta. Next, detecting end parts of the center line of the aorta obtained in this way makes it possible to automatically detect the apex cordis. Further, calculating gradients of pixel values around the center line of the blood vessel to detect a gradient of pixel values corresponding to the shape of the mitral valve makes it possible to automatically detect the tip position of the mitral valve. That is, positions of the blood vessel and the cardiac initial reference points can be automatically detected with use of continuity in signals from blood.

As another concrete example, there is a method of specifying the initial reference points according to a prepared determination unit, expressed by an algorithm, a function or the like, for automatically determining the cardiac initial reference points from volume image data by referring to library files as reference data. For example, a nonlinear determinant of which input is a matrix representing pixel values at respective positions of volume image data and outputs are position vectors of the initial reference points such as the apex cordis and the tip position of the mitral valve by referring to the library files can be made. Alternatively, a function which returns a position vector, corresponding to a part to be specified based on information such as statistics values and/or probability distributions with regard to pixel values at respective positions in volume image data expressed by a matrix as an input, with referring to the library files can be made.

As the reference data, the library file data can be used. The library file data is based on anatomical knowledge with regard to features of respective parts of a heart and many pieces of information with regard to cardiac features acquired from other objects as described above. That is, the reference section calculation part 40A can specify the initial reference points by an algorithm using the library files stored in the library file storage unit 44 as reference data. Using the library files for automatically specifying the initial reference points makes it possible to set the remaining reference cross sections according to a relatively simple procedure based on subsequent analytic processing, e.g., a procedure for setting the reference cross sections standardized by an institute or the like.

The cardiac morphological characteristics depend on characteristics of an object such as a body shape and a kind of disease. Therefore, using library files processed and generated statistically for respective characteristics of objects such as body shapes and kinds of diseases in order to determine the initial reference points automatically makes it possible to calculate the cardiac initial reference points more exactly according to detail characteristics of an object.

Moreover, a priority may be previously determined for whether the method for calculating the initial reference points with referring the library files stored in the library file storage unit 44 or the analytical one by signal processing based on anatomical knowledge is used. In this case, the proper calculation method can be selected according to conditions.

For example, the first algorithm including analytic signal processing based on anatomical knowledge may be used preferentially for detection processing of the cardiac initial reference points and the second algorithm with referring to the library files based on many pieces of examination image data of objects may be used secondly for detail detection processing of the cardiac initial reference points in case where the initial reference points could not be detected with sufficient accuracy by the first algorithm. Alternatively, the opposite order may be adopted. That is, one algorithm can be changed into the other algorithm according to a detection accuracy of the initial reference points.

In addition, there is also a method for calculating the cardiac initial reference points exactly by correction of the initial reference points calculated provisionally with an automatic calculation algorithm which performs two dimensional pattern matching. The correction can be performed by pattern matching or detection of characterizing points.

In this method, the apex cordis and the tip position of the mitral valve on an initial section are firstly calculated from volume image data by an automatic calculation algorithm which performs two dimensional pattern matching between the volume image data and reference data on the initial section.

Next, an expression representing a position of the first long axis passing through the apex cordis and the tip position of the mitral valve on the initial section is calculated. However, the initial section is a section provisionally set for the two dimensional pattern matching in the automatic calculation algorithm Therefore, accuracy in calculation of the respective positions of the apex cordis, the tip of the mitral valve and the first long axis is rough. Accordingly, the initial section is rotated with a central focus on the first long axis having rough accuracy.

Next, a rotation angle of the initial section at which the resolution of the section becomes the highest is detected based on the frames of axial image data (volume image data) before the isotropic transformation processing. Specifically, the resolution of the rotated section image data differs according to a normal direction of the rotated section because the rotated section image data has anisotropy.

Accordingly, a section corresponding to a high resolution is detected for detecting the apex cordis and the tip position of the mitral valve with high accuracy.

Next, positions of the apex cordis and the mitral valve are detected by two dimensional pattern matching between the axial image data and the reference data on the detected section corresponding to the high resolution or detection of characterizing positions in pixel values of the axial image data. Then, an expression representing a position of the second accurate long axis passing through the apex cordis and the tip position of the mitral valve on the section corresponding to the high resolution is calculated.

As described above, an accurate position of the long axis can be calculated by two pattern matching with detection of a section corresponding to a high resolution.

As a method other than each example described above, the initial reference positions may be calculated by performing two or three dimensional pattern matching under a known way such as processing with a cross-correlation value or fitting for zing differences. In this case, template data representing positions of points and/or outlines for pattern matching may be prepared. Preparing many pieces of template data for respective diseases and characteristics of objects makes it possible to calculate the initial reference points with higher accuracy. The template data can be also made based on anatomical knowledge and/or past pieces of image data of objects similarly to the library files.

Next, in the step S5 of FIG. 3, the reference section calculation part 40A calculates reference cross section image data by pattern matching and/or detecting characterized points on various sections generated on the basis of the long axis or the initial reference points of the heart. For the pattern matching of the reference cross section image data, an algorithm of which inputs are information indicating the position of the long axis and volume image data and outputs are pixel values of the reference cross section image data can be prepared. On the other hand, the library files stored in the library file storage unit 44 can be used as reference data for detecting processing of characterized points.

Figure 6:
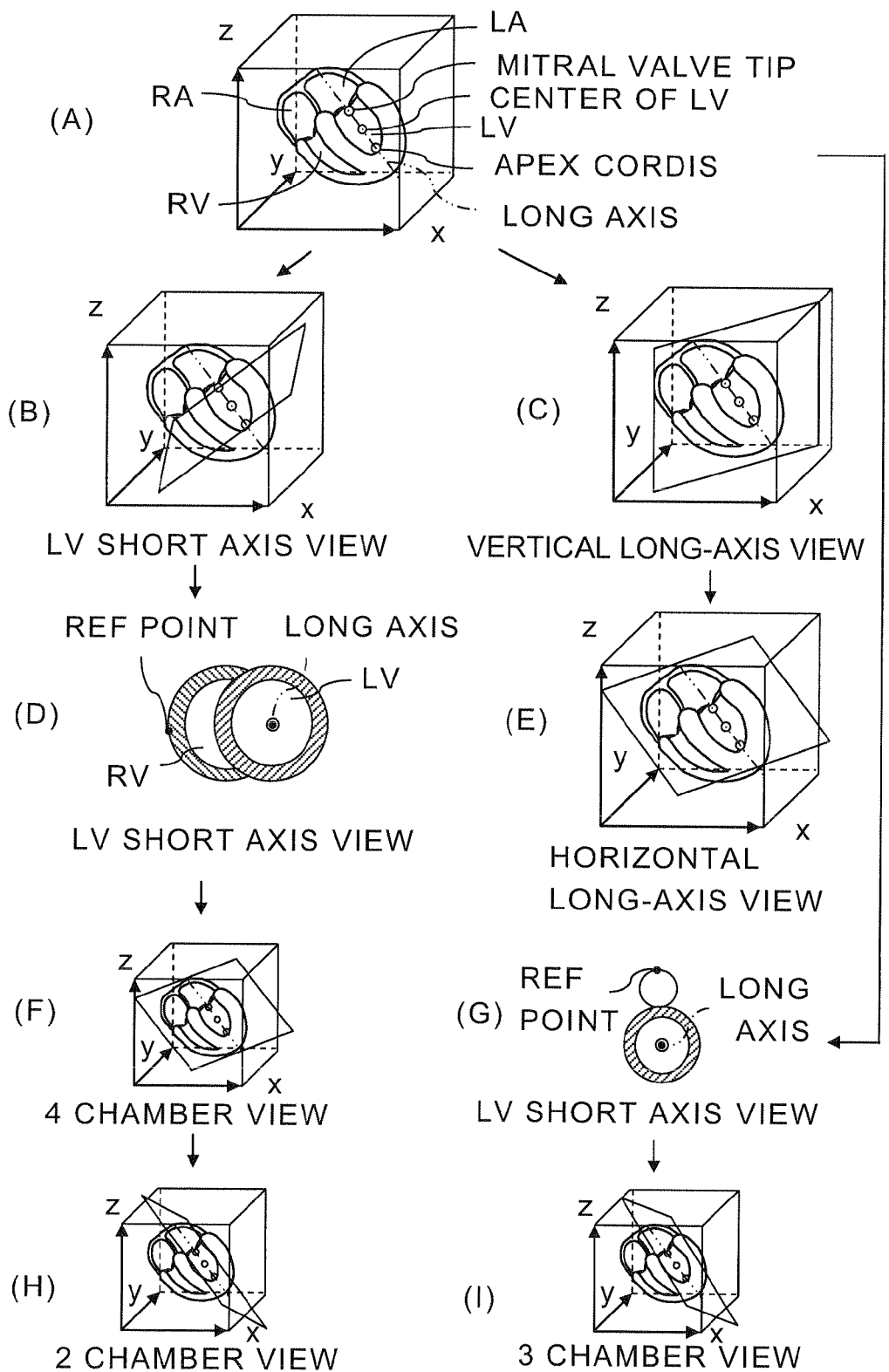
FIG. 6 is a chart showing a flow for generating the reference cross section images based on the cardiac long axis in the reference section calculation part shown in FIG. 2.

FIG. 6 is a chart showing a flow for generating the reference cross section images based on the cardiac long axis in the reference section calculation part 40A shown in FIG. 2.

As shown in FIG. 6(A), the six frames of reference cross section image data can be automatically generated from the volume image data, in which the cardiac long axis is detected, by calculation.

Specifically, LV short axis view data can be generated as image data of a section orthogonal to the long axis. In many cases, the section image passing through the center of the LV is chosen as the LV short axis view as shown in FIG. 6(B).

Meanwhile, vertical long axis view data can be generated as image data of the section involving the long axis and parallel to the z axis (the body axis) as shown in FIG. 6(C). Further, horizontal long axis view data can be generated as image data of the section orthogonal to the vertical long axis view and involving the long axis as shown in FIG. 6(E).

In addition, a position of the end point of the RV can be detected as a reference point by known detection processing of a characterized point, such as pattern matching or pixel value determination, to the LV short axis view data shown in FIG. 6(D). Herewith, 4 chamber view data can be generated as image data of the section involving the long axis and passing through the reference point marked on the end point of the RV as shown in FIG. 5(F). The 4 chamber view is the reference cross section image on which the four chambers of the LV, the LA, the RV and the RA are depicted.

Subsequently to generation of the 4 chamber view data, 2 chamber view data can be generated as image data of the section orthogonal to the 4 chamber view and involving the long axis as shown in FIG. 6(H). The 2 chamber view is the reference cross section image on which the two chambers of the LV and the LA are depicted.

Further, on a LV short axis view generated for the vicinity of the cardiac base part, not the RV but the LV discharge canal is depicted as shown in FIG. 6(G). Therefore, a position of the end point of the LV discharge canal can be detected as a reference point by known detection processing of a characterized point, such as pattern matching or pixel value determination, to the LV short axis view data shown in FIG. 6(G). Herewith, 3 chamber view data can be generated as image data of the section involving the long axis and passing through the reference point marked on the end point of the LV discharge canal as shown in FIG. 6(I). The 3 chamber view is the reference cross section image on which the three chambers of the LV, the LA and the LV discharge canal are depicted.

As described above, detecting characterized points on the necessary positions in the LV short axis view data to mark the detected points as reference points makes it possible to generate the 2 chamber view data, the 3 chamber view data and the 4 chamber view data automatically and sequentially.

Note that, only necessary frames of the reference cross section image data selected by a user may be generated instead of generation of the six frames of the reference cross section image data. With referring to the example shown in FIG. 6, spatial positional information of at least one section of the 4 chamber view, the 3 chamber view and the 2 chamber view can be calculated after calculation of that of the LV short axis view based on the long axis connecting the tip of the mitral valve with the apex cordis. In case of calculating all, spatial positional information of sections of the 4 chamber view, the 2 chamber view and the 3 chamber view can be calculated in a sequential order.

Further, positions of characterized points such as the end point of the RV and/or the end point of the LV discharge canal may be automatically detected according to a prepared algorithm together with the positions of the apex cordis and the tip of the mitral valve in the step S4. Furthermore, a position of a tricuspid valve may be recognized to be detected instead of the end point of the RV. In this case, some frames of reference cross section image data can be generated without detection processing of a characterized point in the step S5.

When the reference cross section image data has been generated by the reference section calculation part 40A, the reference cross section image data or vector information indicating positions and directions of the reference cross sections in the volume image data is written in the reference section storage unit 45 as spatial positional information with regard to the cardiac reference cross sections.

Next, in the step S6, the imaging section setting part 40B positions an imaging part for cardiac imaging. For that purpose, the imaging section setting part 40B displays a single reference cross section image or plural reference cross section images, together with a screen for setting an imaging section, to be referred to for positioning the imaging part on the display unit 34. That is, the imaging section setting part 40B displays reference section images of the heart, calculated from the frames of the axial image data based on the positional information of the cardiac reference cross sections, on the display unit 43. Subsequently, the imaging section setting part 40B performs positioning of an imaging part for imaging through the displayed reference section images of the heart. The display conditions including kinds, directions, sizes and resolutions of reference cross section images to be displayed on the display unit 34 can be preset according to a frequency of usage of a user and the like in the imaging section setting part 40B.

Specifically, the imaging section setting part 40B outputs reference cross section image data to the display unit 34 in case where the imaging section setting part 40B has obtained the reference cross section image data as it is from the reference section storage unit 45. Meanwhile, the imaging section setting part 40B reads the volume image data from the image data storage unit 43 in case where the imaging section setting part 40B has obtained vector information indicating positions and directions of reference cross sections from the reference section storage unit 45. Subsequently, the imaging section setting part 40B generates the frames of reference cross section image data corresponding to the vector information by MPR (multi planar reconstruction) processing of the volume image data.

For example, in case of depicting an image for observing a static period of the coronary by imaging, cardiac reference cross section images are displayed on the display unit 34 for setting a ROI appropriate for observation of a static period of the coronary.

Alternatively, not reference cross section image data itself but desired other section image data generated on the basis of reference cross sections by MPR processing of the volume image data may be displayed as a reference image for positioning on the display unit 34. Specifically, the imaging section setting part 40B automatically calculates image data for setting a ROI in real time by MPR processing of the volume image data and displays the image data generated by the calculation on the display unit 34 in response to an input of positional vector information of a cross section image for setting a ROI in the imaging section setting part 40B with operation of the input device 33 by a user. In addition, image data on the imaging section itself may be also generated by MPR processing to be displayed precedently to imaging.

Some desired frames of section image data, other than the reference cross section image data, generated by MPR processing may be used as new frames of reference cross section image data. For example, instruction for setting a desired frame of cross section image data as a frame of reference cross section image data can be inputted into the imaging section setting part 40B from the input device 33. Therefore, the automatically calculated reference cross section image data can be also corrected with operation of the input device 33.

Specifically, the imaging section setting part 40B can update cardiac reference cross section images displayed on the display unit 34 based on instructions to adjust the cardiac reference cross section images displayed on the display unit 34 into an arbitrary direction when the instructions are inputted from the input device 33. For example, at least one of the apex cordis, the mitral valve, the long axis and the center of LV can be displayed as a cardiac anatomical characterized part together with cardiac reference cross section images on the display unit 34. Then, the imaging section setting part 40B can update the reference cross section images in conjunction with movement of the characterized part when instructions to move the characterized part are inputted from the input device 33 to the imaging section setting part 40B.

That is, cardiac reference cross section images can be automatically calculated based on positional information of characterized parts to be displayed on the display unit 34. In this case, it can also be said that it is positional information of movable cardiac characterized parts displayed on the display unit 34 rather than spatial positional information of cardiac reference cross sections that is automatically calculated based on frames of section image data such as frames of axial image data by the reference section calculation part 40A. Of course, positional information of cardiac characterized parts can be also calculated based on volume data such as 3D imaging data as well as frames of section image data.

MPR images including the reference cross section images can be displayed as thumbnail images so as to be able to be selected. In this case, vector information may be added to thumbnail image data as incidental information. Therefore, dragging a thumbnail image displayed on the display unit 34 and dropping the dragged thumbnail image on one of pulse sequences displayed as choices for imaging with operation of the input device 33 such as a mouse can be assigned to set a cross section specified by the vector information incidental to the dragged and dropped thumbnail image to a data acquisition section by the corresponding pulse sequence, for example.

That is, when the imaging section setting part 40B has acquired information for selecting a thumbnail image and an imaging sequence from the input device 33, the imaging section setting part 40B sets a section specified by a vector incidental to the selected thumbnail image data to a section for acquiring MR data and sets a pulse sequence of which type is same with that of the selected pulse sequence to a sequence for imaging.

Alternatively, mutually different reference cross section images themselves or their thumbnail images generated by calculation and/or MPR processing can be displayed on the display unit 34. Then, when information to relate one of reference cross section images with an imaging protocol corresponding to imaging having a various purpose such as cine imaging, late contrast-enhanced imaging, myocardial perfusion imaging, Black Blood imaging, transverse relaxation (T2) weighted imaging, feature imaging of the whole heart or DWI (diffusion weighted imaging) is inputted from the input device 33 to the imaging section setting part 40B, appropriate conditions with regard to slices to be imaged can be displayed on at least one of other reference cross section images. Note that, the conditions with regard to imaging slices include a slice thickness, a slice interval, a gap between slices and a slice coverage (range of slices).

For example, selecting one reference cross section image as an imaging target by an imaging protocol for feature imaging of a whole heart can automatically set slice conditions including a slice coverage covering the whole heart and display the set slice conditions on other reference cross section images crossing with the selected reference cross section image. Alternatively, selecting one reference cross section image as an imaging target by a protocol for cine imaging can display the selected reference cross section or a few parallel sections of which center is the selected reference cross section as an imaging slice or imaging slices on other reference cross section images.

The data acquisition sections by the imaging sequences may be preset according to imaging purposes as well as be manually set with operation of the input device 33. For example, data acquisition sections may be preset so as to be assigned with imaging sequences automatically and subsequently.

Note that, the vector information indicating positions and directions of reference cross sections can be outputted to other medical devices through networks or storage media.

Therefore, the information with regard to the reference cross sections can be used in other medical devices.

The imaging condition setting unit 40 can automatically set various imaging conditions as well as the data acquisition section. For example, the following imaging conditions are automatically set. Specifically, the imaging condition setting unit 40 automatically determines the longitudinal direction of the imaging part by image processing to set the short direction of the imaging part into the encode direction. Further, the imaging condition setting unit 40 rotates a rectangular FOV (field of view) on a same plane to automatically correct the FOV so that the longitudinal direction of the FOV becomes the longitudinal direction of the heart. Furthermore, the imaging condition setting unit 40 automatically detects the center position of the heart by image processing to automatically adjust the FOV so that the center position of the FOV becomes about the center position of the heart to be imaged. The imaging condition setting unit 40 also measures the size of the heart to be the imaging part automatically. Then, imaging condition setting unit 40 expands the FOV so that the imaging part lies in the FOV if the imaging part is protruding from the FOV.

Next, in the step S7, an imaging scan is performed to image the imaging part set by the positioning. Specifically, the imaging condition setting unit 40 outputs the imaging conditions including the data acquisition part set by the imaging section setting part 40B to the sequence controller 31. Therefore, MR data for generating cardiac diagnostic image data is acquired from the object P in a flow similarly to that for acquisition of the scout image data and the multi-slice axial image data. Subsequently, image generation part 41A generates diagnostic image data of the object P based on the MR data.

Next, in the step S8, the index generation part 41B adds information for specifying the cardiac reference cross section used for positioning the diagnostic image data to the diagnostic image data as its sorting information. Specifically, the index generation part 41B acquires information identifying the cardiac reference cross section image corresponding to the diagnostic image data from the imaging section setting part 40B and subsequently adds the acquired information identifying the cardiac reference cross section image to the diagnostic image data as incidental information.

Then, frames of diagnostic image data positioned through desired reference cross sections respectively in a similar flow are acquired subsequently. The acquired frames of diagnostic image data are written in the image data storage unit 43. Each frame of diagnostic image data stored in the image data storage unit 43 is appended to the information identifying the corresponding cardiac reference cross section image. Therefore, the frames of diagnostic image data can be sorted out and retrieved with use of the information identifying the reference cross section images as indexes to display a desired frame of diagnostic image data.

As described above, the magnetic resonance imaging apparatus 20 is an apparatus configured to automatically obtain spatial positions of cardiac reference cross sections by calculation based on image data on one or some of simple orthogonal three cross sections such as axial image data and display the reference cross section images, generated by the calculation, for positioning in cardiac imaging. Further, the magnetic resonance imaging apparatus 20 is an apparatus configured to make use of calculation results of reference cross sections, corresponding to frames of diagnostic image data acquired by imaging, as index information of the frames of diagnostic image data.

Therefore, it is not necessary for the magnetic resonance imaging apparatus 20 to repeat positioning and acquisition of reference cross section image data, which has been performed precedently to a cardiac imaging scan conventionally. Consequently, troublesome manual operations by a user can be avoided to acquire cardiac reference cross section image data in a shorter time.

In addition, the magnetic resonance imaging apparatus 20 can automatically detect cardiac characterized points according to a predetermined algorithm to calculate spatial positions of cardiac reference cross sections with uniform accuracy using the detected characterized points. Therefore, accuracy in positioning can be kept without depending on cardiac anatomical knowledge and skill of a user and characteristics of each object. Further, the magnetic resonance imaging apparatus 20 can sort pieces of diagnostic image data using pieces of calculated image data, corresponding to arbitrary cross sections, generated by calculation without acquiring image data actually. Therefore, a way to sort pieces of diagnostic image data is not restricted and it becomes possible to classify diagnostic images according to a preference of a user.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, frames of axial image data may be acquired in both static periods $\Delta T1$ of cardiac systoles and static periods $\Delta T2$ of cardiac diastoles shown in FIG. 5, respectively. In this case, spatial positional information for the first cardiac reference cross sections based on the frames of axial image data corresponding to the static period of the cardiac diastole and that for the second one corresponding to the static period of the cardiac systole can be calculate respectively. Therefore, the more satisfactorily calculated positional information for the reference cross sections showing the higher accuracy can be selected from the first and the second positional information for the reference cross sections. In other words, if timings for acquiring MR signals for axial image data, acquiring axial image data again can be prevented. Furthermore, a period for acquiring MR signals need not be increased as such for that purpose.

Further, cardiac imaging has been described mainly in the above mentioned embodiment. However, automatic detection of reference positions and calculation of reference cross section images can be performed for aortal imaging in a similar way.

Further, a function to tutor an operation of apparatus, positioning work and the like to users and/or a function to appraise skills of users may be provided with the magnetic resonance imaging apparatus 20 on the assumption of a user who is not skilled in operation of apparatus, positioning work and/or the like. For example, when multi-slice image data and reference cross section images are acquired manually by a user, appraisal information can be made for a skill of the user by matching a necessary time for an operation, accuracy in a reference cross section and the like with respective appraisal standard indexes. The index for accuracy in a reference cross section can be defined as a deviation amount between a manually acquired reference cross section and a calculated one for example. These functions can be provided with magnetic resonance imaging apparatus 20 as functions of the computer 32.

What is claimed is:

1. A magnetic resonance imaging (MRI) apparatus comprising:
    a static magnetic field generator;
    gradient magnetic field coils;
    at least one radio frequency coil;
    a display; and
    a control system including at least one control computer coupled to control said display, said gradient magnetic field coils, and said at least one radio frequency coil, said control computer being configured to:
    control said gradient magnetic field coils and said at least one radio frequency coil to acquire volume image data including a heart from an object;
    automatically calculate spatial-positional locations of pre-determined anatomical features of the heart based on the acquired volume image data;
    automatically generate a reference section image of the heart by:
        generating a reference section of the heart at a spatial-positional location corresponding to the calculated spatial-positional locations of pre-determined anatomical features of the heart,
        identifying, from the acquired volume image data, imaging data with spatial-positional locations that correspond to the spatial-positional location of the reference section, and
        generating the reference section image of the heart by forming the identified imaging data into an image;
    control the display to display the generated reference section image of the heart;
    set a position of an imaging plane for subsequent cardiac imaging corresponding to a position of the displayed reference section image of the heart; and
    control said gradient magnetic field coils and said at least one radio frequency coil to acquire a cardiac image of the set imaging plane within the heart of said object.

2. The magnetic resonance imaging apparatus of claim 1, wherein said control computer is configured to calculate the spatial-positional location of pre-determined anatomical features by automatically detecting the spatial-positional locations of pre-determined anatomical features by
    a first automated process based on the acquired volume image data and pre-stored anatomical knowledge data, and then by
    a second automated process based on detection accuracy of the positional information of the reference section achieved by the first process and at least one of pre-stored anatomical knowledge and frames of cardiac feature image data of hearts from other objects.

3. The magnetic resonance imaging apparatus of claim 1, wherein said control computer is configured to generate the reference section by:
    generating picks for positions of the reference section,
    automatically narrowing down the picks by referring to reference data generated from at least one of (a) pre-stored anatomical knowledge data and (b) frames of cardiac feature image data of the hearts from other objects, and
    automatically specifying the position of the reference section based on the acquired volume image data by signal processing based on pre-stored anatomical knowledge data after automatically narrowing down the picks.

4. The magnetic resonance imaging apparatus of claim 1, wherein said control computer is configured to calculate the spatial-positional location of pre-determined anatomical features based on the acquired volume image data by automatically detecting the spatial-positional locations of pre-determined anatomical features by
    a first process including signal processing based on pre-stored anatomical knowledge data, or
    a second process referring to pre-stored reference data generated from at least one of (a) pre-stored anatomical knowledge data and (b) cardiac feature image data of hearts from other objects.

5. The magnetic resonance imaging apparatus of claim 1, wherein said control computer is configured to calculate the spatial-positional location of pre-determined anatomical features based on the acquired volume image data by
    calculating the spatial-positional locations of pre-determined anatomical features as vector information.

6. The magnetic resonance imaging apparatus of claim 1, further comprising a manually operated input device for selecting a thumbnail image, wherein the control computer is configured to:
    automatically generate different and display different reference section images of the heart as thumbnails by:
        generating different reference sections of the heart at different spatial-positional locations corresponding to the calculated spatial-positional locations,
        identifying, from the acquired volume image data, different imaging data with different spatial-positional locations that correspond to the different spatial-positional locations of the reference section,
        generating the different reference section images of the heart as thumbnails by forming the identified different imaging data into different images, and
        controlling the display to display the different reference section images as thumbnail images;
    receive a selection of one of the displayed thumbnails from the manually operated input device; and
    set a data acquisition pulse sequence to acquire magnetic resonance data for subsequent cardiac imaging in accordance with the position of the reference section image of the heart corresponding to a selected thumbnail.

7. The magnetic resonance imaging apparatus of claim 1, further comprising a manual input device configured to input information relating to an imaging protocol, wherein the control computer is configured to:
    automatically generate and display different reference section images by:
        generating different reference sections of the heart at different spatial-positional locations corresponding to the calculated spatial-positional locations,
        identifying, from the acquired volume image data, different imaging data with different spatial-positional locations that correspond to the different spatial-positional locations of the reference section,
        generating the different reference section images of the heart as thumbnails by forming the identified different imaging data into different images, and
        controlling the display to display the different reference section images; and
    display a condition on at least one other reference section image indicating a slice to be a target of subsequent cardiac imaging, when information, relating to one of the reference section images with an imaging protocol, is manually inputted from the manual input device.

8. The magnetic resonance imaging apparatus of claim 1, wherein said control computer is further configured:
to add information, identifying the reference section image used for setting the position of the imaging plane, to the acquired cardiac image as sorting information for the acquired cardiac image.

9. The magnetic resonance imaging apparatus of claim 1, wherein said control computer is configured to automatically generate at least three different reference sections of the heart at respectively different spatial-positional locations corresponding to the calculated spatial-positional locations of pre-determined anatomical features of the heart.

10. The magnetic resonance imaging apparatus of claim 1, wherein said control computer is configured to automatically calculate the spatial-positional locations of the pre-determined anatomical features by
generating at least three views of the heart using the acquired volume image data, the at least three views selected from the group consisting of (a) a vertical long-axis view,(b) a horizontal long-axis view, (c) a four chamber long-axis view, (d) a three chamber long-axis view,(e) a two chamber long-axis view and (f) a left ventricle short-axis view, and
using the generated at least three views of the heart to calculate the spatial-positional locations of the pre-determined anatomical features.

11. The magnetic resonance imaging apparatus of claim 1, wherein said control computer is configured to automatically calculate the spatial-positional locations of pre-determined anatomical features by
generating isotropic volume data by preprocessing the acquired volume image data to transform the acquired volume image data into the isotropic data, and
calculating the spatial-positional locations of pre-determined anatomical features based on the generated isotropic volume data.

12. The magnetic resonance imaging apparatus of claim 1, further comprising:
a manually operated input device configured to receive a manually inputted instruction to adjust the reference section image displayed on the display into an arbitrary direction,
wherein said control computer is further configured to automatically update the reference section image displayed on the display based on the received manually inputted instruction, when the instruction is manually inputted from the manually operated input device by moving the reference section in the arbitrary direction,
identifying, from the acquired volume image data, imaging data with spatial-positional locations that correspond to the spatial-positional location of the moved reference section,
generating an updated reference section image by forming the identified imaging data into an image, and
controlling the display to display the generated updated reference section image.

13. The magnetic resonance imaging apparatus of claim 10, wherein said control computer is further configured to
control the display to display an anatomically characterized part of the heart together with the reference section images,
receive a manually inputted instruction to move the characterized part, and
automatically update the reference section images in conjunction with movement of the characterized part when the instruction to move the characterized part is received by
moving the reference section in conjunction with movement of the characterized part,
identifying, from the acquired volume image data, imaging data with spatial-positional locations that correspond to the spatial-positional location of the moved reference section,
generating an updated reference section image by forming the identified imaging data into an image, and
controlling the display to display the generated updated reference section image.

14. The magnetic resonance imaging apparatus of claim 11, wherein said control computer is further configured to control the display to display at least one of an apex cordis, a mitral valve, a long axis and a center of a left ventricle as an anatomically characterized part.

15. The magnetic resonance imaging apparatus of claim 1, further comprising an electrocardiogram generator providing an electrocardiogram,
wherein said control computer is configured to control said gradient magnetic field coils and said at least one radio frequency coil to acquire said volume image data by a single shot magnetic resonance imaging sequence synchronized with the electrocardiogram.

16. The magnetic resonance imaging apparatus of claim 1, further comprising an electrocardiogram generator providing an electrocardiogram,
wherein said control computer is configured to control said gradient magnetic field coils and said at least one radio frequency coil to acquire the volume image data as a plurality of frames of section image data by acquiring one frame of section image data between adjacent two or three reference waves of the electrocardiogram.

17. The magnetic resonance imaging apparatus of claim 1, wherein said control computer is configured to control said gradient magnetic field coils and said at least one radio frequency coil to acquire said volume image data by acquiring said volume image data at same cardiac time phases of multiple cardiac cycles.

18. The magnetic resonance imaging apparatus of claim 1, further comprising an electrocardiogram generator providing an electrocardiogram,
wherein said control computer is configured to control said gradient magnetic field coils and said at least one radio frequency coil to acquire said volume image data by acquiring said volume image data at constant delay times of multiple cardiac cycles relative reference waves of the electrocardiogram.

19. The magnetic resonance imaging apparatus of claim 1, wherein said control computer is configured to control said gradient magnetic field coils and said at least one radio frequency coil to acquire said volume image data by acquiring said volume image data during static periods of systoles or static periods of diastoles of the heart.

20. The magnetic resonance imaging apparatus of claim 1, wherein the control computer is configured to:
control said gradient magnetic field coils and said at least one radio frequency coil to acquire said volume image data by acquiring first and second sets of said volume image data during static periods of systoles and static periods of diastoles of the heart respectively;

calculate spatial-positional locations of pre-determined anatomical features based on the acquired volume image data by:
    automatically calculating first spatial-positional locations of pre-determined anatomical features based on the acquired first set of volume image data corresponding to static periods of systoles, and
    automatically calculating second spatial-positional locations of pre-determined anatomical features based on the acquired second set of volume image data corresponding to static periods of diastoles; and
generate the reference section of the heart by generating first and second reference sections of the heart by:
    automatically calculating spatial positional information of the first reference section of the heart based on the calculated first spatial-positional locations of pre-determined anatomical features, and
    automatically calculating spatial positional information of the second reference section of the heart based on the calculated second spatial-positional locations of pre-determined anatomical features.

21. The magnetic resonance imaging apparatus of claim 1, wherein said control computer is configured to:
    automatically calculate spatial-positional locations of pre-determined anatomical features of the heart based on the acquired volume image data by calculating spatial-positional locations of a long-axis connecting a tip of a mitral valve with an apex cordis; and
    generate the reference section of the heart at a spatial-positional location corresponding to the calculated spatial-positional locations of pre-determined anatomical features of the heart by:
        automatically calculating spatial-positional information of a section of a left ventricle short-axis view based on the calculated spatial-positional locations of the long-axis connecting a tip of a mitral valve with an apex cordis, and
        automatically calculating spatial-positional information for at least one section of a four chamber long-axis view, a three chamber long-axis view, and a two chamber long-axis view as said reference section of the heart based on the calculated spatial-positional information of the section of the left ventricle short-axis view.

22. The magnetic resonance imaging apparatus of claim 1, wherein said control computer is configured to:
    automatically calculate spatial-positional locations of pre-determined anatomical features of the heart based on the acquired volume image data by calculating spatial-positional locations of a long-axis connecting a tip of a mitral valve with an apex cordis; and
    generate the reference section of the heart at a spatial-positional location corresponding to the calculated spatial-positional locations of pre-determined anatomical features of the heart by:
        automatically calculating spatial-positional information of a section of a left ventricle short-axis view based on the calculated spatial-positional locations of the long-axis connecting a tip of a mitral valve with an apex cordis, and
        automatically calculating spatial-positional information for sections of a four chamber long-axis view, a two chamber long-axis view, and a three chamber long-axis view in a sequential order as said reference section of the heart based on the calculated spatial-positional information of the section of the left ventricle short-axis view.

23. The magnetic resonance imaging apparatus of claim 1, wherein said control computer is configured to:
    automatically calculate spatial-positional locations of pre-determined anatomical features of the heart based on the acquired volume image data by:
        calculating spatial-positional locations of a right ventricle in case of functional evaluation of the right ventricle, and
        calculating spatial-positional locations of a valve in case of a functional evaluation of the valve; and
    generate the reference section of the heart at a spatial-positional location corresponding to the calculated spatial-positional locations of pre-determined anatomical features of the heart by:
        automatically calculating spatial-positional information for a reference section consisting of a section crossing the right ventricle, based on the calculated spatial-positional locations of the right ventricle, as said reference section of the heart in the case of functional evaluation of the right ventricle, and
        automatically calculating spatial-positional information of a reference section consisting of a section passing through the valve, based on the calculated spatial-positional locations of the valve, as said reference section in the case of functional evaluation of the valve.

24. The magnetic resonance imaging apparatus of claim 1, wherein:
    the control computer is configured to control said gradient magnetic field coils and said at least one radio frequency coil to acquire the volume image data by acquiring frames of section image data as the volume image data.

25. The magnetic resonance imaging apparatus of claim 1, further comprising:
    an electrocardiogram generator providing an electrocardiogram,
    wherein the control computer is configured to control said gradient magnetic field coils and said at least one radio frequency coil to acquire the volume image data by acquiring the volume image data in synchronization with the electrocardiogram.

26. A magnetic resonance imaging (MRI) apparatus as in claim 1 wherein the control computer is configured to:
    generate a plurality of reference section images of the heart in different directions based on the volume image data by:
    generating a plurality of reference sections in the different directions based on the volume image data,
    identifying, from the acquired volume image data, a plurality of imaging data with spatial-positional locations that correspond to the spatial-positional locations of the plurality of reference sections respectively, and
    generating the plurality of reference section images of the heart by forming the identified plurality of imaging data into a plurality of images;
    control the display to display the generated plurality of reference section images of the heart in different directions;
    set a position of another imaging plane for subsequent cardiac imaging based on positions of the displayed plurality of reference section images of the heart in different directions; and
    control said gradient magnetic field coils and said at least one radio frequency coils to acquire a cardiac image of said another imaging plane within the heart of said object.

27. A magnetic resonance imaging (MRI) control apparatus comprising:
at least one computer configured to:
control gradient magnetic field coils and at least one radio frequency coil of a magnetic resonance imaging apparatus to acquire volume image data including a heart of an object;
automatically detect a position of at least one anatomical part of the heart based on the acquired volume image data;
automatically calculate a position of at least one reference section of the heart, based on the automatically detected anatomical part of the heart;
automatically generate at least one reference section image of the heart by:
identifying, from the acquired volume image data, imaging data with positions that correspond to the position of the at least one reference section, and
generating the at least one reference section image of the heart by forming the identified imaging data into at least one image;
control a display of said magnetic resonance imaging apparatus to display said at least one reference section image of the heart;
set at least one imaging plane for imaging corresponding to a position of the displayed at least one reference section image of the heart; and
control said gradient magnetic field coils and said at lest one radio frequency coil of said magnetic resonance imaging apparatus to subsequently acquire at least one cardiac image of the at least one imaging plane within the heart.

28. The magnetic resonance imaging apparatus of claim 27, wherein the at least one computer is configured with reference image section kind presets which allow a kind of the displayed reference section image to be preset.

29. The magnetic resonance imaging apparatus of claim 27, wherein the at least one computer is configured to:
store library data representing a determination reference, for specifying the anatomical part, as a combination of parameters; and
detect the position of the at least one anatomical part of the heart further based on the stored library data.

30. A magnetic resonance imaging (MRI) control apparatus comprising:
at least one computer configured to:
control gradient magnetic field coils and at least one radio frequency coil of a magnetic resonance imaging apparatus to acquire volume image data including a heart of an object;
automatically calculate a position of at least one reference section of a heart based on the acquired volume image data;
automatically generate at least one reference section image of the heart by:
identifying, from the acquired volume image data, imaging data with positions that correspond to the position of the at least one reference section, and
generating the at least one reference section image of the heart by forming the identified imaging data into at least one image;
control a display of said magnetic resonance imaging apparatus to display said at least one reference section image of the heart;
set an imaging plane for imaging corresponding to a position of the displayed reference section image of the heart;
control said gradient magnetic field coils and said at least one radio frequency coil of said magnetic resonance imaging apparatus to subsequently acquire at least one cardiac image of the imaging plane within the heart;
receive, from an input device, a manually inputted instruction to update the displayed reference section image; and
update the displayed reference section image, based on the received instruction.

31. A magnetic resonance imaging (MRI) method comprising:
acquiring volume image data including a heart from an object;
automatically calculating spatial-positional locations of pre-determined anatomical features of the heart based only on the acquired volume image data;
automatically calculating spatial-positional locations of a reference section of the heart based on the calculated spatial-positional locations of the pre-determined anatomical features of the heart;
generating a reference section image of the heart by:
identifying, from the acquired volume image data, imaging data with spatial-positional locations that correspond to the spatial-positional locations of the reference section, and
generating the reference section image of the heart by forming the identified imaging data into an image;
displaying the reference section image of the heart on a display;
setting a position of an imaging plane for imaging corresponding to a position of the displayed reference section image of the heart; and
subsequently acquiring an MR cardiac image of the imaging plane within the heart.

32. A magnetic resonance imaging (MRI) method as in claim 31 wherein:
a plurality of reference section images of the heart are generated in different directions based on the volume image data by:
generating a plurality of reference sections in the different directions based on the volume image data,
identifying, from the acquired volume image data, a plurality of imaging data with spatial-positional locations that correspond to the spatial-positional locations of the plurality of reference sections respectively, and
generating the plurality of reference section images of the heart by forming the identified plurality of imaging data into a plurality of images;
the generated plurality of reference section images of the heart in different directions are displayed on a display;
the position of another imaging plane for subsequent cardiac imaging is set based on positions of the displayed plurality of reference section images of the heart in different directions; and
a cardiac image of said another imaging plane within the heart of said object is acquired.

* * * * *